(12) United States Patent
Fitzpatrick

(10) Patent No.: US 12,227,474 B2
(45) Date of Patent: Feb. 18, 2025

(54) METHODS OF PRODUCING AND RECOVERING LEVULINIC ACID

(71) Applicant: Biofine Technology LLC, Brookline, MA (US)

(72) Inventor: Stephen W. Fitzpatrick, Framingham, MA (US)

(73) Assignee: Biofine Technology, LLC, Brookline, MA (US)

( * ) Notice: Subject to any disclaimer, the term of this patent is extended or adjusted under 35 U.S.C. 154(b) by 0 days.

(21) Appl. No.: 18/609,781

(22) Filed: Mar. 19, 2024

(65) Prior Publication Data

US 2024/0376036 A1 Nov. 14, 2024

Related U.S. Application Data

(60) Provisional application No. 63/466,191, filed on May 12, 2023.

(51) Int. Cl.
C07C 51/48 (2006.01)

(52) U.S. Cl.
CPC .................................. *C07C 51/48* (2013.01)

(58) Field of Classification Search
CPC .............................. C07C 51/48; C07C 59/185
See application file for complete search history.

(56) References Cited

U.S. PATENT DOCUMENTS

| 3,212,933 A | 10/1965 | Hess et al. |
| 7,378,549 B2 | 5/2008 | Ayoub |
| 11,299,447 B2 | 4/2022 | De Haan et al. |
| 2006/0201879 A1 | 9/2006 | Leendert et al. |
| 2014/0323759 A1* | 10/2014 | Fitzpatrick .............. C07C 51/44 562/515 |
| 2021/0253508 A1* | 8/2021 | López Fernández .... B01D 3/10 |

FOREIGN PATENT DOCUMENTS

| CN | 101 875 605 | 11/2010 |
| WO | WO2013078391 | * 5/2013 |
| WO | WO 2017/064069 | 4/2017 |

OTHER PUBLICATIONS

International Search Report and Written Opinion in International Appln. No. PCT/US2024/020569, mailed on Jul. 9, 2024, 21 pages.
Rajendaren et al., "A Review of The Methods for Levulinic Acid Separation and Extraction," Biomass Conversion and Biorefinery, Oct. 17, 2022, 15 pages.
Ji et al., "Integrated Production of Furfural and Levulinic Acid From Corncob In a One-Pot Batch Reaction Incorporating Distillation Using Step Temperature Profiling," RSC Advances, Sep. 25, 2017, 7(73):46208-14.
Christensen et al., "Renewable oxygenate blending effects on gasoline properties," Energy & Fuels, Oct. 20, 2011, 25(10):4723-33, 2 pages (abstract only).
Joback et al., "Estimation of pure-component properties from group-contributions," Chemical Engineering Communications, Jul. 1, 1987, 57(1-6):233-43, 1 page (abstract only).
Morales et al., "Beta zeolite as an efficient catalyst for the synthesis of diphenolic acid (DPA) from renewable levulinic acid," Catalysis Today, Dec. 1, 2023, 424:113801.
Thomas et al., "Membrane distillation research & implementation: Lessons from the past five decades," Separation and Purification Technology, Dec. 22, 2017, 189:108-27, 8 pages (abstract only).

* cited by examiner

*Primary Examiner* — Yevgeny Valenrod
*Assistant Examiner* — Blaine G Doletski
(74) *Attorney, Agent, or Firm* — Fish & Richardson P.C.

(57) ABSTRACT

The disclosure relates to methods of producing and recovering levulinic acid.

25 Claims, 3 Drawing Sheets

METHODS OF PRODUCING AND RECOVERING LEVULINIC ACID

CROSS-REFERENCE TO RELATED APPLICATION

This application claims the benefit under 35 U.S.C. § 120 to U.S. Patent Application U.S. Ser. No. 63/466,191, filed on May 12, 2023. The entire contents of the prior application are hereby incorporated by reference herein.

FIELD

This disclosure relates to methods of producing and recovering levulinic acid.

BACKGROUND

Solvent extraction, such as with an alcohol, can be used during the synthesis and isolation of levulinic acid.

SUMMARY

The disclosure relates to methods of producing and recovering levulinic acid, such as producing levulinic acid from cellulose feedstocks (e.g., lignocellulose).

These methods include a reactive back extraction step where after the extraction of levulinic acid into an organic phase (e.g., an alcohol such as hexanol), the organic phase is contacted with water. The levulinic acid is extracted into the aqueous phase which can be concentrated to a relative high concentration of levulinic acid (e.g., at least 60 wt. %, at least 70 wt. %, at least 80 wt. %, at least 90 wt. % levulinic acid) with relatively little (e.g., no) dehydration and/or polymerization of levulinic acid derivatives such as beta angelicalactone. Additionally, at least a portion of levulinic acid converted to an ester during the organic phase extraction can be reconverted into levulinic acid.

The methods can produce levulinic acid with higher yields relative to some other methods of producing levulinic acid. The methods can convert at least a portion of an ester of levulinic acid (e.g., hexyl levulinate) formed during the solvent extraction step back to levulinic acid. The methods can produce levulinic acid with a relatively simple purification process relative to certain other methods. The methods can reduce (e.g., prevent) the formation of undesirable lactone, tarry and/or polymeric byproducts during a separation, purification and/or dehydration step.

The methods can be used to generate derivative products of levulinic acid such as an ester useful as fuel (e.g., ethyl levulinate) and/or monomers relatively efficiently and/or with higher yield relative to certain other methods of generating derivative products of levulinic acid. The methods can consume paper pulp, waste paper, waste wood and/or forest waste to generate fuel (e.g., ethyl levulinate). The methods can generate fuel (e.g., ethyl levulinate) with net negative carbon dioxide emissions. Thus, the methods can generate fuel and other derivatives relatively efficiently and/or with lower emissions relative to certain other methods of generating fuel.

In a first aspect the disclosure provides a method of producing levulinic acid, including contacting a first solution including levulinic acid and an acid with an organic solvent; extracting at least a portion of the levulinic acid from the first solution into the organic solvent forming a second solution including the levulinic acid and the organic solvent; contacting the second solution with water; and extracting at least a portion of the levulinic acid from the second solution into the water forming a third solution including the levulinic acid and the water. The organic solvent includes an alcohol.

In some embodiments, the alcohol includes a $C_6$ to $C_8$ alcohol. In some embodiments, the alcohol includes hexanol, heptanol, octanol and/or isoamyl alcohol.

In some embodiments, the acid includes sulfuric acid nitric acid, hydrochloric acid, hydrobromic acid, and/or p-toluene sulfonic acid.

In some embodiments, the second solution further includes an ester of levulinic acid and contacting the second solution with water converts at least a portion of the ester of levulinic acid into levulinic acid. In some embodiments, the alcohol includes hexanol and the ester of levulinic acid includes hexyl levulinate. In some embodiments, the alcohol includes heptanol and the ester of levulinic acid includes heptyl levulinate. In some embodiments, the alcohol includes octanol and the ester of levulinic acid includes octyl levulinate. In some embodiments, the alcohol includes isoamyl alcohol and the ester of levulinic acid includes isoamyl levulinate.

In some embodiments, the first solution includes a volatile component, and the method further includes removing the volatile component from the first solution. In some embodiments, the volatile component includes formic acid, acetic acid and furfural.

In some embodiments, the method further includes contacting a precursor material with the acid to form the first solution. In some embodiments, the acid is sulfuric acid, nitric acid, hydrochloric acid, hydrobromic acid, and/or p-toluene sulfonic acid. In some embodiments, the precursor material includes cellulose, lignocellulose, furfural, furfuryl alcohol, a sugar, and/or maleic anhydride.

In some embodiments, the method further includes evaporating a portion of the water in the third solution. In some embodiments, a concentration of levulinic acid in the third solution is from 60 wt. % to 90 wt. % after evaporation.

In some embodiments, the method further includes converting at least a portion of the levulinic acid into a member selected from the group consisting of ethyl levulinate, aminolevulinic acid, succinic acid, acrylic acid, 3-hydroxy propionic acid, and diphenolic acid.

In some embodiments, the method further includes separating the first solution and the second solution.

In some embodiments, the method further includes separating the second solution and the third solution.

In some embodiments, a ratio of water to second solution is from 0.25:1 to 5:1 water:second solution.

In a second aspect, the disclosure provides a method of recovering levulinic acid, including contacting a first solution including an organic solvent and levulinic acid and/or an ester of levulinic acid with water, and forming a second solution including levulinic acid and water.

In certain embodiments, the first solution includes the ester of levulinic acid and contacting the first solution with water converts at least a portion of the ester of levulinic acid into levulinic acid.

In certain embodiments, the organic solvent includes an alcohol.

In certain embodiments, the ester of levulinic acid includes an ester formed from the reaction of levulinic acid and the alcohol. In certain embodiments, the alcohol includes a $C_6$ to $C_8$ alcohol. In certain embodiments, the alcohol includes hexanol, heptanol, octanol, and/or isoamyl alcohol. In certain embodiments, the alcohol includes hexanol and the ester of levulinic acid includes hexyl levulinate.

In certain embodiments, the alcohol includes heptanol and the ester of levulinic acid includes heptyl levulinate. In certain embodiments, the alcohol includes octanol and the ester of levulinic acid includes octyl levulinate. In some embodiments, the alcohol includes amyl or isoamyl alcohol and the ester of levulinic acid includes amyl or isoamyl levulinate.

In certain embodiments, the method further includes evaporating a portion of the water in the second solution. In certain embodiments, a concentration of levulinic acid in the second solution is from 60 wt. % to 90 wt. % after evaporation.

In certain embodiments, the method further includes converting at least a portion of the levulinic acid into ethyl levulinate, aminolevulinic acid, succinic acid, acrylic acid, 3-hydroxy propionic acid, and/or diphenolic acid.

In certain embodiments, the method further includes separating the first solution and the second solution.

In certain embodiments, a ratio of water to first solution is from 0.25:1 to 5:1 water:first solution.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
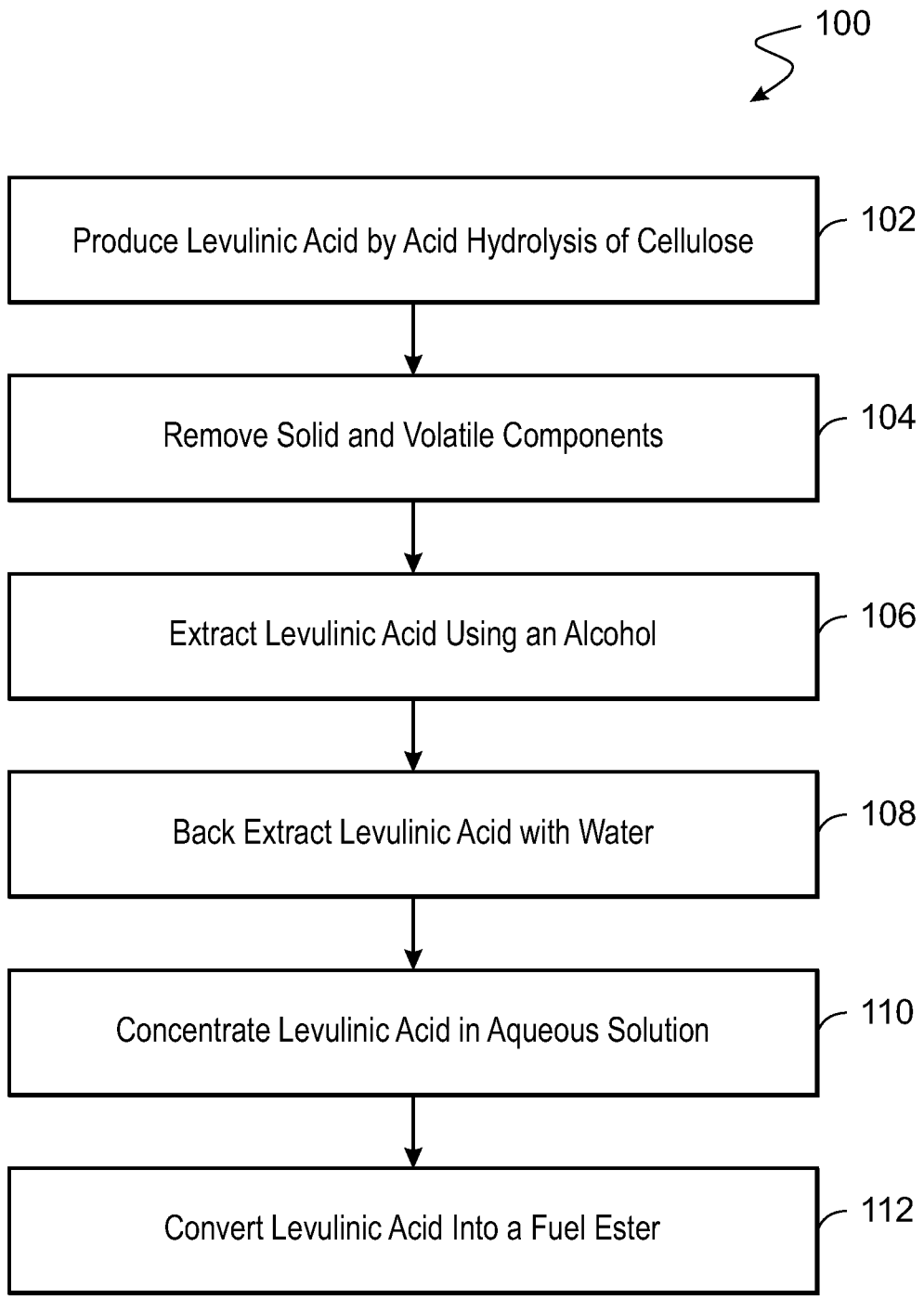
FIG. 1 depicts a flow chart for a method.

FIG. 1 depicts a flowchart for a method 100. In step 102, levulinic acid is produced from a cellulose and/or lignocellulose feedstock by acid hydrolysis. Levulinic acid can also be produced from furfural via furfuryl alcohol or from sugars like glucose, sucrose or cellobiose, or from maleic anhydride by oxidation. The cellulose and/or lignocellulose can be derived from paper pulp, waste paper, waste wood and/or forest waste (e.g., softwood waste).

In step 104, the solid and volatile components are removed resulting in a first mixture including levulinic acid and the acid (e.g., sulfuric acid). The volatile components can include formic acid, acetic acid, and furfural. The solid components can be removed using any appropriate method, such as by filtration, centrifugation or sedimentation. Filtration can be performed with a filter (e.g., a 10 micron nominal pore size coarse filter cloth), a membrane, by centrifugation, or by gravity sedimentation. Smaller colloidal particulate can be further removed by use of finer pore size membrane filters such as those used for microfiltration, ultrafiltration or nanofiltration. The volatile components can be removed using any appropriate method, such as by steam stripping. In some embodiments, the steam stripping can be performed using excess steam or waste heat at atmospheric pressure and 100° C. and a stripping factor (V/F) of at most 0.9. In some embodiments, the stream stripping can be performed under vacuum at 100 mm Hg and a stripping factor (V/F) as low as 0.16 (e.g., as low as 0.1).

In step 106, the levulinic acid is extracted from the first solution using solvent extraction. The first solution is contacted by an organic solvent that includes an alcohol. The alcohol can be any $C_6$ to $C_8$ alcohol. Examples of the alcohol include hexanol, heptanol, octanol and isoamyl alcohol. Without wishing to be bound by theory, the alcohol should have a relatively low solubility in the aqueous phase, which can be achieved with a sufficiently long chain hydrocarbon (e.g., at least six carbons). The alcohol should also have a relatively high volatility allowing removal by steam stripping. Hexanol is relatively inexpensive and demonstrates both sufficiently low water solubility and sufficiently high volatility. The step 106 results in the formation of a second solution (an organic phase) that includes levulinic acid and the organic solvent as at least a portion of the levulinic acid is extracted into the organic phase. In general, the levulinic acid distributes between the aqueous and organic phases. The aqueous and organic phases can be separated by gravity separation or centrifugal force. The acid (e.g., sulfuric acid) remains in the aqueous phase. The remaining aqueous phase (raffinate) containing sulfuric acid and/or non-extracted levulinic acid is separated from the second solution and recycled back to the hydrolysis reactor where it is mixed with new feedstock. At least a portion of the levulinic acid in the second solution (the organic phase) is converted to an ester of levulinic acid in the second solution. For example, if the organic solvent includes hexanol, at least a portion of the levulinic acid is converted to hexyl levulinate. As another example, if the organic solvent includes heptanol, at least a portion of the levulinic acid is converted to heptyl levulinate. As an additional example, if the organic solvent includes octanol, at least a portion of the levulinic acid is converted to octyl levulinate. As a further example, if the organic solvent includes amyl or isoamyl alcohol, at least a portion of the levulinic acid is converted to amyl or isoamyl levulinate.

In step 108, the levulinic acid is back-extracted from the second solution into water by contacting the second solution with water, forming a third solution including levulinic acid and water. Furthermore, at least a portion of the ester of levulinic acid in the second solution is converted by reaction into levulinic acid and extracted into the water. In some embodiments, at least 19 (e.g., at least 20, at least 25, at least 30, at least 35, at least 40, at least 45) % and/or at most 49 (e.g., at most 45, at most 40, at most 35, at most 30, at most 25, at most 20) % of the ester of levulinic acid (e.g., hexyl levulinate) in the second solution is converted to levulinic acid. In some embodiments, at least 54 (e.g., at least 55, at least 60, at least 65, at least 70, at least 75, at least 80, at least 85) % and/or at most 88 (e.g., at most 85, at most 80, at most 75, at most 70, at most 65, at most 60, at most 55) % of the ester of the levulinic acid is transferred to the third solution. The step 108 can be performed in a continuous countercurrent mode, a continuous co-current mode or in a batch mixing mode.

In step 110, the levulinic acid in the third solution is concentrated by evaporating a portion of the water. After concentrating, the concentration of levulinic acid is at least 60 (e.g., at least 65, at least 70, at least 75, at least 80, at least 85, at least 90) wt. % and/or at most 95 (e.g., at most 90, at most 85, at most 80, at most 75, at most 70, at most 65) wt. %. Without wishing to be bound by theory, it is believed that the third solution can be concentrated with relatively little (e.g., no) dehydration of levulinic acid (e.g., to form lactones) relative to concentrating levulinic acid in other solvents (e.g., an organic solvent). The step 110 can be performed in a vacuum concentration apparatus. In certain embodiments, the step 110 is performed in a vacuum concentration apparatus at 100 mm mercury absolute pressure. Additionally, alcohol that remains in the aqueous extract can be separated from the condensed vapor during the evaporation process and be recycled in the step 106.

In step 112, the levulinic acid is converted into a high-value product. Examples of the high value product include an ester useful as fuel, such as ethyl levulinate, aminolevulinic acid, succinic acid, acrylic acid, 3-hydroxy propionic acid, diphenolic acid, and other monomers. The conversion of levulinic acid to ethyl levulinate can be performed by reacting the levulinic acid with ethanol. Excess ethanol can be removed by distillation. The step 112 can yield ethyl levulinate with a purity of at least 97 (e.g., at least 97.5, at least 98, at least 98.5, at least 99, at least 99.5, at least 99.8, at least 99.9) %.

Figure 2:
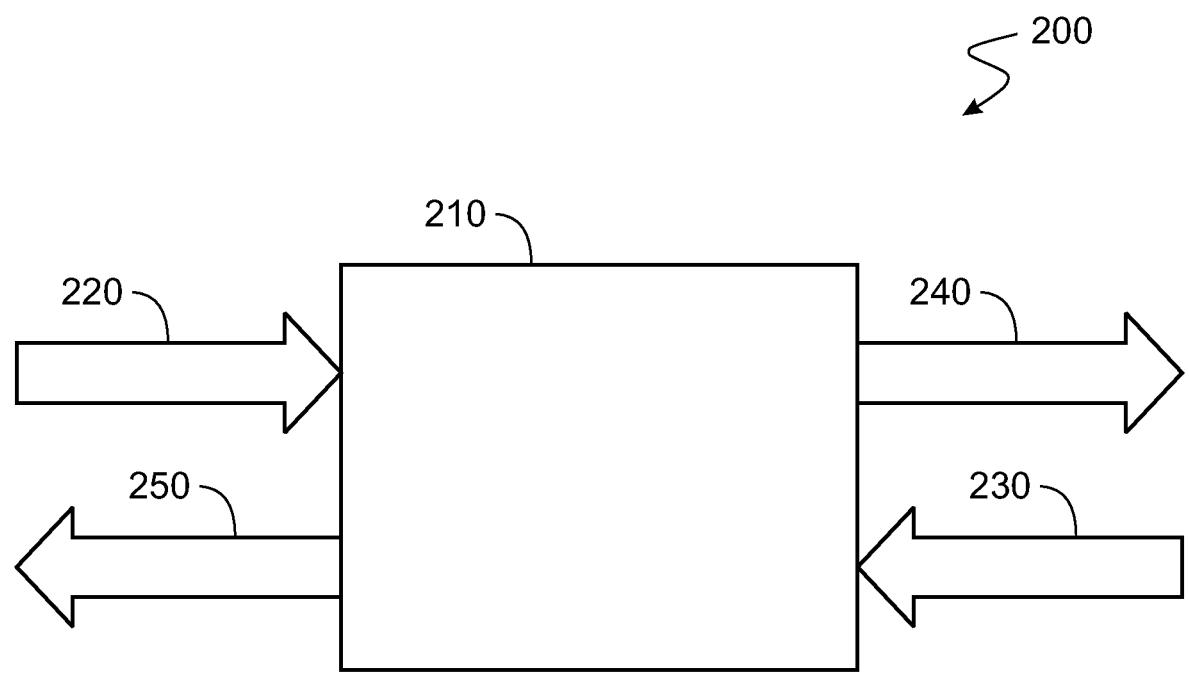
FIG. 2 depicts a schematic for a system that includes a mixer.

In some embodiments, the step 102 can generate levulinic acid at a concentration of at least 7 (e.g., at least 8, at least 9, at least 10, at least 11, at least 12, at least 13, at least 14, at least 15, at least 16, at least 17, at least 18, at least 19, at least 20, at least 21, at least 22, at least 23, at least 24) wt. % and/or at most 25 (e.g., at most 24, at most 23, at most 22, at most 21, at most 20, at most 19, at most 18, at most 17, at most 16, at most 15, at most 14, at most 13, at most 12, at most 11, at most 10, at most 9, at most 8) wt. %. Examples of the acid used include a mineral acid such as sulfuric acid, nitric acid, hydrochloric acid, hydrobromic acid, and p-toluene sulfonic acid. In some embodiments, the concentration of acid is at least 2 (e.g., at least 3, at least 4, at least 5, at least 6, at least 7, at least 8, at least 9) wt. % and/or at most 10 (e.g., at most 9, at most 8, at most 7, at most 6, at most 5, at most 4, at most 3) wt. %. The step 102 can be performed in a continuous back-mixed reactor. The step 102 can be performed at a temperature of at least 185 (e.g., at least 190, at least 195, at least 200, at least 205° C.) and/or at most 210 (e.g., at most 205, at most 200, at most 195, at most 190° C.) Without wishing to be bound by theory, it is believed that a temperature below 195° C. and above 185° C. can increase the yield of the coproduct formic acid which is a produced with levulinic acid. The step 102 can be performed for at least 10 (e.g., at least 15, at least 20, at least 25) minutes and/or at most 30 (e.g., at most 25, at most 20, at most 15) minutes. In some embodiments, the step 102 can be performed in a continuous back-mixed reactor with 3.5% sulfuric acid at 195° C. for at most 30 minutes FIG. 2 depicts a schematic for a system 200 that can be used in the step 108. An organic feed stream 220 and a fresh water stream 230 are contacted in a mixer 210. The organic feed stream 220 generally includes hexanol, levulinic acid and hexyl levulinate. In the mixer 210, at least a portion of the hexyl levulinate from the organic feed stream 220 is converted into levulinic acid by reaction with the water. Additionally, at least a portion of the levulinic acid (free levulinic acid from the organic feed stream 220 and/or levulinic acid formed from the hydrolysis) of hexyl levulinate enters the aqueous phase. An organic output stream 240 and an aqueous output stream exit the mixer 210. The organic output stream 240 includes hexanol and can further include unhydrolyzed hexyl levulinate and/or levulinic acid. The aqueous output stream 250 includes water and levulinic acid. Hexyl levulinate is insoluble in the aqueous phase, thus the aqueous output stream 250 does not include hexyl levulinate. The organic feed stream 220 corresponds to the second solution and the aqueous output stream 250 corresponds to the third solution in the step 108. Hexyl levulinate can stay with the organic phase be and recycled back to the step 106.

The mixer 210 can be a continuous multistage centrifugal contactor, such as a Podbielniak machine, a continuous mixer-settler, such as a Robatel machine, or a stirred tank batch contactor where phases are mixed and allowed to settle in the same vessel. Gravity settlement can also be used to separate the aqueous output stream 250 from the organic output stream 240. Liquid filled towers (e.g., with packing or plates) can also be used for separate the aqueous output stream 250 from the organic output stream 240. Flows of the organic feed stream 220 and a fresh water stream 230 can be counter current, co-current and/or can be batch-contacted.

The concentration of levulinic acid in aqueous output stream 250 (corresponding to the third solution generated in the step 108) can be at least 7 (e.g., at most 7.5, at most 8, at least 8.5, at least 9, at least 9.5) wt. % and/or at most 12 (e.g., at most 11.5, at most 11, at most 10.5, at most 10, at most 9.5, at most 9, at most 8.5) wt. %. The ratio the fresh water stream 230 and the organic feed stream 220 (corresponding to the amount of water added to the second solution in the step 108) is at least 0.25:1 (e.g., at least 0.3:1, at least 0.4:1, at least 0.5:1, at least 0.6:1, at least 0.7:1, at least 0.75:1, at least 0.8:1, at least 0.9:1, at least 1:1, at least 1.5:1, at least 2:1, at least 2.5:1, at least 3:1, at least 3.5:1, at least 4:1, at least 4.5:1) and/or at most 5:1 (e.g., at most 4.5:1, at most 4:1, at most 3.5:1, at most 3:1, at most 2.5:1, at most 2:1, at most 1.5:1, at most 1:1, at most 0.9:1, at most 0.8:1, at most 0.75:1, at most 0.7:1, at most 0.6:1, at most 0.5:1, at most 0.4:1, at most 0.3:1) water:organic phase. Without wishing to be bound by theory, it is believed that the amount of water used should be minimized while maintaining a relatively high level of extraction of levulinic acid. Due to the extraction with water at least a portion (e.g., at least 50% and/or at most 90%) of the levulinic acid from the organic feed stream 220 can be extracted into the aqueous output stream 250 given the appropriate number of extraction stages (e.g., at least four) and/or the appropriate ratio of the fresh water stream 230 to the organic feed stream 220 (e.g., 1.4).

Figure 3:
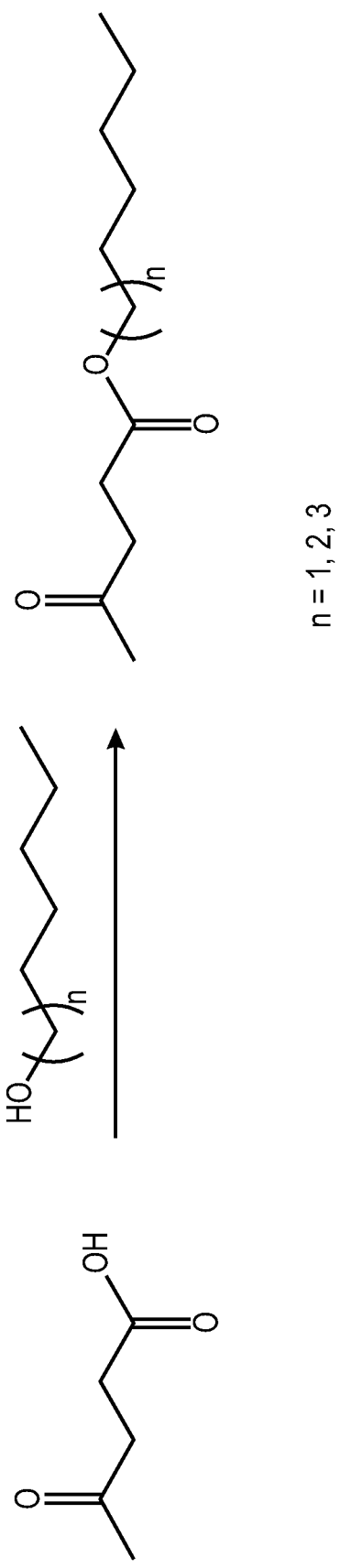
FIG. 3 depicts a reaction scheme.

FIG. 3 depicts a reaction scheme for the conversion of levulinic acid into an ester in the presence of an alcohol. When n=1, levulinic acid is converted into hexyl levulinate in hexanol. When n=2, levulinic acid is converted into heptyl levulinate in heptanol. When n=3, levulinic acid is converted into octyl levulinate in octanol. As discussed above, without wishing to be bound by theory, it is believed that the back extraction of levulinic acid from the alcohol (e.g., hexanol, heptanol, octanol) to an aqueous phase can convert at least a portion of the ester (e.g., hexyl levulinate, heptyl levulinate, octyl levulinate) to levulinic acid.

In some embodiments, the aqueous phase does not include sulfuric acid. In some embodiments, the aqueous phase contains sulfuric acid (e.g., a catalytic amount of sulfuric acid). Without wishing to be bound by theory, it is believed that the presence of sulfuric acid may aid in the hydrolysis of hexyl levulinate to levulinic acid.

EXAMPLES

Example 1

51 kg of a hexanol solution containing 2.29 kg (4.5 wt. %) levulinic acid and an estimated 1.82 kg (2.1 wt. %) hexyl levulinate was blended with 51 kg of fresh water in a 200 L HDPE drum container. The liquids were batch-blended by mixing using a 0.25 HP drum mixer with a 2 inch three-blade impellor for 1 hour. The liquids were allowed to settle and separate overnight The top hexanol layer was carefully pumped and skimmed off the top and collected separately using a hose attached to a pump. The lower aqueous layer was then pumped out of the drum and allowed to settle in a separatory funnel. Remaining hexanol was removed by skimming the remaining aqueous phase.

The final mass of the aqueous extract was 50.9 kg and the final mass of the hexanol raffinate was 47.5 kg. The mass balance accountability was found to be 96.5%. The mass of levulinic acid initially introduced in the organic phase was measured by high-pressure liquid chromatography (HPLC) to be 2.29 kg. After separation, analysis of the organic raffinate phase by gas chromatography (GC) indicated that the amount of levulinic acid in the organic phase was 1.002 kg (2.1 wt. %). Analysis of the aqueous extract phase by HPLC indicated that the amount of levulinic acid in the aqueous phase was 1.6 kg (3.12 wt. %). The total quantity of levulinic acid therefore increased from 2.29 kg to 2.59 kg, indicating an increase of 0.3 kg (13%).

The mass of hexyl levulinate in the initial organic phase was estimated by material balance difference to be 1.82 kg. In the reverse extraction, the overall quantity of levulinic acid increased by 296.4 g, indicating that 510.9 g of hexyl levulinate was hydrolyzed. The mass of hexyl levulinate was therefore estimated in the organic raffinate was 1.31 kg (1.82 kg minus 0.51 kg). The aqueous phase was free of hexyl levulinate as hexyl levulinate is insoluble in water. The loss in hexyl levulinate was estimated to be 0.51 kg. The increase in levulinic acid of 0.3 kg closely corresponds to the equivalent loss in hexyl levulinate of 0.51 kg. Thus, the water extraction resulted in the hydrolysis of approximately 28% (0.51/1.82) of the hexyl levulinate in the organic phase. 47.8% of the levulinic acid originally in the organic phase as free and esterified levulinic acid (hexyl levulinate) was extracted into the aqueous phase. The extraction of levulinic acid (47.8%) was surprisingly high for only a single batch extraction stage.

The aqueous extract was then processed through a Buchi R-220 20 L floor-standing rotovap vacuum evaporator. The rotovap removed a portion of the water to concentrate the aqueous phase. After concentrating the aqueous phase by a factor of 10, the evaporation was temperately halted and the concentrate was filtered through a 1.5 micron microfiber glass filter. A small amount of precipitate was filtered out. The concentrate was further concentrated to a final concentration of 947.6 g/L levulinic acid (approximately 90 wt. % levulinic acid). The concentrate also contained 10 wt. % formic acid trace amounts of sulfuric acid. Concentrations were determined by HPLC. The levulinic acid did not undergo any appreciable loss due to polymerization. The maximum loss of levulinic acid over the evaporation was 5.4% The aqueous phase was able to be concentrated to a relatively high concentration of levulinic acid and low enough for water concentration to be suitable for use as a raw material for further chemical conversion, such as esterification (e.g., conversion to ethyl levulinate by reaction with ethanol).

Example 2-Podbeilniak

Several aqueous extraction experiments were carried out using a pilot scale Podbeilniak A-25 Centrifugal Contactor (POD). The extraction machine carried out mixer-settler operations using centrifugal force and rotary pumping action to replace gravitational force for separation and multi-stage counter-current mixing. The unit had two inlet nozzles and two outlet nozzles. The body of the machine spins to cause centrifugal mixing and settling of the immiscible organic and aqueous phases. The A-25 POD is designed to be the equivalent to approximately four ideal stages of mixing and settling.

In a series of experiments, the POD was used with a range of ratios of flowrates of organic feed to aqueous extract. The organic feed (organic input stream), which contained levulinic acid and hexyl levulinate dissolved in hexanol, was fed into the inlet nozzle of the POD at a range of flowrates via a calibrated dosing pump. The freshwater extraction phase (fresh water input stream) was simultaneously fed to the other inlet nozzle.

In each stage within the machine, the aqueous extract phase was continuously mixed with the water-immiscible organic (hexanol) phase and immiscible layers were separated by centrifugal force. The hexanol phase contained, as dissolved components, both esterified levulinic acid (hexyl levulinate) and free unesterified levulinic acid. It was desired to extract as much free and esterified levulinic acid as possible. Since hexyl levulinate is insoluble in the aqueous phase, the hexyl levulinate in the organic phase was hydrolyzed to yield levulinic acid that was extracted into the aqueous phase.

The volumetric flow of organic feed was varied between 0.405 and 0.597 liters per minute (LPM). The aqueous (fresh water) extract phase was fed at flowrates ranging from 0.467 to 0.8 LPM. The flowrate ratios of organic feed to aqueous extract ranged from 1.13 to 1.37. The levulinic acid and hexyl levulinate concentrations in the organic feed were 35.4 g/L and 79.8 g/L, respectively, over all seven experiments, as measured by GC. The outlet concentrations in the organic raffinate (organic output stream) ranged from 5.41 to 5.89 g/L for levulinic acid and from 54.52 to 57.44 g/L for hexyl levulinate as measured by GC. Outlet concentrations in the aqueous extract ranged from 30.87 g/L to 35.15 g/L for levulinic acid as measured by HPLC. The hexyl levulinate was insoluble in aqueous media. The parameters and contents of the streams are summarized in Table 1. The mass flow was calculated based on the flow meter calibration curve. The amount in grams of levulinic acid and hexyl levulinate was calculated by multiplying the concentration in g/L by the volumetric flow. The total levulinate corresponds to the amount of levulinic acid and hexyl levulinate. The total levulinic acid equivalent was calculated as the amount of levulinic acid and the amount of hexyl levulinate scaled using the molecular weights of levulinic acid and hexyl levulinate.

TABLE 1

Summary of input and output streams

| | Exp. 1 | Exp. 2 | Exp. 3 | Exp. 4 | Exp. 5 | Exp. 6 | Exp. 7 |
|---|---|---|---|---|---|---|---|
| Organic input stream | | | | | | | |
| Volumetric flow (LPM) | 0.405 | 0.414 | 0.597 | 0.584 | 0.571 | 0.573 | 0.423 |
| Mass flow (g/min) | 327.24 | 334.51 | 482.38 | 471.87 | 461.37 | 462.98 | 341.78 |
| Levulinic acid (g/L) | 35.35 | 35.35 | 35.35 | 35.35 | 35.35 | 35.35 | 35.35 |
| Hexyl levulinate (g/L) | 79.8 | 79.8 | 79.8 | 79.8 | 79.8 | 79.8 | 79.8 |

TABLE 1-continued

Summary of input and output streams

|  | Exp. 1 | Exp. 2 | Exp. 3 | Exp. 4 | Exp. 5 | Exp. 6 | Exp. 7 |
|---|---|---|---|---|---|---|---|
| Levulinic acid (g) | 14.3 | 14.6 | 21.1 | 20.6 | 20.2 | 20.3 | 15.0 |
| Hexyl levulinate (g) | 32.32 | 33.04 | 47.64 | 46.60 | 45.57 | 45.73 | 33.76 |
| Total levulinate (g) | 46.64 | 47.67 | 68.74 | 67.25 | 65.75 | 65.98 | 48.71 |
| Total levulinic acid equivalent (g) | 33.06 | 33.80 | 48.74 | 47.67 | 46.61 | 46.78 | 34.53 |
| Fresh water input stream | | | | | | | |
| Volumetric flow (LPM) | 0.497 | 0.467 | 0.788 | 0.8 | 0.779 | 0.779 | 0.519 |
| Water (g) | 497 | 467 | 788 | 800 | 779 | 779 | 519 |
| Organic output stream | | | | | | | |
| Volumetric flow (LPM) | 0.393 | 0.4 | 0.578 | 0.566 | 0.553 | 0.555 | 0.409 |
| Mass flow (g/min) | 317.544 | 323.2 | 467.02 | 457.33 | 446.82 | 448.44 | 330.47 |
| Levulinic acid (g/L) | 5.61 | 5.89 | 5.69 | 5.77 | 5.59 | 5.59 | 5.41 |
| Hexyl levulinate (g/L) | 56.35 | 56.63 | 56.87 | 54.52 | 57.36 | 55.97 | 57.44 |
| Levulinic acid (g) | 2.20 | 2.36 | 3.29 | 3.27 | 3.09 | 3.10 | 2.21 |
| Hexyl levulinate (g) | 22.15 | 22.65 | 32.87 | 30.9 | 31.7 | 31.1 | 23.5 |
| Total levulinate (g) | 24.4 | 25.0 | 36.2 | 34.1 | 34.8 | 34.2 | 25.7 |
| Total levulinic acid equivalent (g) | 15.0 | 15.5 | 22.4 | 21.2 | 21.5 | 21.1 | 15.8 |
| Water output stream | | | | | | | |
| Volumetric flow (LPM) | 0.51 | 0.5 | 0.809 | 0.82 | 0.799 | 0.798 | 0.533 |
| Mass flow (g/min) | 510 | 500 | 809 | 820 | 799 | 798 | 533 |
| Levulinic acid (g/L) | 33.58 | 34.73 | 31.22 | 30.87 | 31.87 | 31.36 | 35.15 |
| Levulinic acid (g) | 17.1 | 17.4 | 25.3 | 25.3 | 25.5 | 25.0 | 18.7 |

Table 2 summarizes the results of the experiments. In all experiments, the percentage breakdown of hexyl levulinate ranged from 30% to 34% and the fraction of total levulinic acid extracted into the aqueous phase ranged from 51% to 55% of the levulinic acid equivalent entering the machine. The aqueous phase had not only hydrolyzed a significant portion of the hexyl levulinate fed to the unit but had extracted a relatively high percentage of the available levulinic acid as an aqueous extract.

TABLE 2

Summary of results

|  | Exp. 1 | Exp. 2 | Exp. 3 | Exp. 4 | Exp. 5 | Exp. 6 | Exp. 7 |
|---|---|---|---|---|---|---|---|
| Aq./Org. flow ratio | 1.23 | 1.13 | 1.32 | 1.37 | 1.36 | 1.36 | 1.23 |
| Levulinic acid in (g) | 14.3 | 14.6 | 21.1 | 20.6 | 20.2 | 20.3 | 15.0 |
| Levulinic acid out (g) | 19.3 | 19.7 | 28.5 | 28.6 | 28.6 | 28.1 | 20.9 |
| Levulinic acid created (g) | 5.0 | 5.1 | 7.4 | 7.9 | 8.4 | 7.9 | 6.0 |
| Levulinic acid created (%) | 15 | 15 | 15 | 17 | 18 | 17 | 17 |
| Hexyl levulinate hydrolyzed (g) | 10.2 | 10.4 | 14.8 | 15.7 | 13.8 | 14.7 | 10.3 |
| Hexyl levulinate hydrolyzed (%) | 31 | 31 | 31 | 34 | 30 | 32 | 30 |
| Levulinic acid extracted (%) | 54 | 51 | 52 | 53 | 54.6 | 55 | 54.3 |
| Overall mass balance (%) | −1 | −4 | −1 | −1 | −1 | −1 | −1 |

Contact with the aqueous phase appeared to both hydrolyze the hexyl levulinate and extract the resulting levulinic acid together with the free levulinic acid. Given the availability of only four stages, extraction of levulinic acid by this technique results in a high percentage of levulinic acid being extracted into the aqueous extract phase.

Example 3-Podbeilniak

Several aqueous extraction experiments were carried out using a pilot scale Podbeilniak A-25 Centrifugal Contactor (POD), as described in Example 2.

The volumetric flow of organic feed hexanol was varied between 0.60 and 0.62 LPM. The aqueous (fresh water) extract phase was fed at volumetric flows ranging from 0.63 to 0.66 LPM. Inlet flows were fed by calibrated metering pumps. The flowrate volume ratios of organic feed to aqueous extract ranged from 1.0 to 1.1. The outlet flows were measured by timed volume collection. The outlet flow for the organic raffinate ranged from 0.61 to 0.63 LPM and the outlet flow for the aqueous extract ranged from 0.61 to 0.65 LPM. The overall mass balance in all tests was 98.9% or better. Summaries of the streams are presented in Table 3. The results are summarized in Table 4.

TABLE 3

Summary of input and output streams

|  | Exp. 1 | Exp. 2 | Exp. 3 | Exp. 4 |
|---|---|---|---|---|
| Organic input stream | | | | |
| Volumetric flow (LPM) | 0.6 | 0.62 | 0.6 | 0.6 |
| Mass flow (g/min) | 484.8 | 500.96 | 484.8 | 484.8 |
| Levulinic acid (g/L) | 37.6 | 37.6 | 32.19 | 32.19 |
| Hexyl levulinate (g/L) | 2.89 | 2.89 | 1.57 | 1.57 |
| Levulinic acid (g/min) | 22.56 | 23.31 | 19.31 | 19.31 |

TABLE 3-continued

Summary of input and output streams

|  | Exp. 1 | Exp. 2 | Exp. 3 | Exp. 4 |
|---|---|---|---|---|
| Hexyl levulinate (g/min) | 1.73 | 1.79 | 0.94 | 0.94 |
| *Fresh water input stream* | | | | |
| Volumetric flow (LPM) | 0.65 | 0.63 | 0.66 | 0.66 |
| Mass flow (g/min) | 650 | 630 | 660 | 660 |
| *Organic output stream* | | | | |
| Volumetric flow (LPM) | 0.61 | 0.63 | 0.61 | 0.61 |
| Mass flow (g/min) | 492.88 | 509.04 | 492.88 | 492.88 |
| Levulinic acid (g/L) | 6.27 | 6.39 | 5.33 | 5.32 |
| Hexyl levulinate (g/L) | 1.5 | 1.46 | 1.22 | 1.23 |
| Levulinic acid (g/min) | 3.82 | 4.03 | 3.25 | 3.25 |
| Hexyl levulinate (g/min) | 0.92 | 0.92 | 0.74 | 0.75 |
| *Water output stream* | | | | |
| Volumetric flow (LPM) | 0.64 | 0.61 | 0.64 | 0.65 |
| Mass flow (g/min) | 640 | 610 | 640 | 650 |
| Levulinic acid (g/L) | 27.13 | 27.39 | 24.24 | 24.3 |
| Levulinic acid (g/min) | 17.36 | 16.71 | 15.51 | 15.80 |

TABLE 4

Summary of results

|  | Exp. 1 | Exp. 2 | Exp. 3 | Exp. 4 |
|---|---|---|---|---|
| Aq./Org. flow ratio (VOLUME) | 1.1 | 1.0 | 1.1 | 1.1 |
| Hexyl levulinate hydrolyzed (g) | 0.82 | 0.87 | 0.20 | 0.19 |
| Hexyl levulinate hydrolyzed (%) | 47 | 49 | 21 | 20 |
| Levulinic acid extracted (%) | 74 | 69 | 78 | 80 |
| Overall mass balance (%) | 0.2 | 1.1 | 1.0 | 0.2 |

Example 4-ROBATEL

Aqueous extraction experiments were carried out using a pilot scale ROBATEL SX 6-0 mixer-settler unit. The unit includes four sequential mixer-settler stages grouped together in a single module. In each stage, the aqueous extract phase was continuously mixed with the water-immiscible organic (hexanol) phase and allowed to separate by gravity. The hexanol phase contained both esterified levulinic acid (hexyl levulinate) and free levulinic acid. It was desired to extract as much free and esterified levulinic acid as possible. Since hexyl levulinate is insoluble in the aqueous phase the hexyl levulinate in the organic phase should be hydrolyzed to yield levulinic acid that can be extracted into the aqueous phase.

An organic mixture containing levulinic acid and hexyl levulinate dissolved in hexanol was fed to the inlet nozzle of the ROBATEL unit by dosing pump at a calibrated flowrate of 1.31 liters per minute (LPM). The organic mixture contained 70.7 g/L of levulinic acid and 15.3 g/L of hexyl levulinate as measured by GC. Fresh water was fed to the other inlet nozzle of the ROBATEL unit using a dosing pump at a calibrated rate of 1.63 LPM. Outlet flows of organic and aqueous phases from the unit were measured using timed volume collection. The unit was allowed to reach equilibrium by allowing three unit volumes of aqueous and organic phases to flow through the unit at a constant flowrate. The approximate unit volume was 225 L. Once at steady state the flowrates of the organic and aqueous outlet streams were measured and samples of both streams were analyzed. The overall mass balance closure over the entire test was 97.4%. The outflowing organic stream was found to have 2.84 g/L of levulinic acid and 12.45 g/L of hexyl levulinate by gas chromatography. The outflowing aqueous stream was analyzed by HPLC and found to have 57.8 g/L of levulinic acid and no hexyl levulinate, which is insoluble in the aqueous phase. A summary of the streams is presented in Table 5.

TABLE 5

Summary of input and output streams

| Organic input stream | |
|---|---|
| Volumetric flow (LPM) | 1.31 |
| Mass flow (kg/min) | 1.06 |
| Levulinic acid (g/min) | 93 |
| Hexyl levulinate (g/min) | 20.0 |
| Total free and esterified LA in (g/min) | 104.6 |
| *Fresh water input stream* | |
| Volumetric flow (LPM) | 1.63 |
| Mass flow (g/min) | 1.630 |
| *Organic output stream* | |
| Volumetric flow (LPM) | 1.33 |
| Mass flow (g/min) | 1.075 |
| Levulinic acid (g/min) | 3.78 |
| Hexyl levulinate (g/min) | 16.56 |
| Total free and esterified LA out (g/min) | 13.4 |
| *Water output stream* | |
| Volumetric flow (LPM) | 1.59 |
| Mass flow (g/min) | 1.590 |
| Levulinic acid (g/min) | 91.9 |

Calculation of the hexyl levulinate entering and leaving the unit indicated a loss of hexyl levulinate of 3.1 grams per minute. This represents the hydrolysis of 16% of the hexyl levulinate entering the unit in the organic phase. The aqueous phase leaving the unit extracted 88% of the free or esterified levulinic acid entering the unit. The overall mass balance closure was 97.4%

Contact with the aqueous phase appeared to accomplish both hydrolysis of the hexyl levulinate and extraction of the resulting levulinic acid together with the free levulinic acid. The aqueous phase had not only hydrolyzed a significant portion of the hexyl levulinate fed to the unit but has extracted a high percentage of the available levulinic acid into the aqueous solution given that the unit consists of only four mixer-settler stages.

Example 5-ROBATEL

Aqueous extraction experiments were carried out using a ROBATEL SX 6-0 mixer-settler unit as descried in Example 4.

In each test a water-immiscible hexanol solution of levulinic acid and hexyl levulinate was extracted with fresh water. The hexanol inlet volumetric flows ranged from 0.55 to 0.84 LPM and the freshwater feed volumetric flows ranged from 0.71 to 1.11 LPM. Ratios of the flowrates of organic feed to aqueous extract ranged from 1.2 to 1.5. Both feeds were input via calibrated dosing pumps. Outlet flows were measured by timed volume collection. The outlet flows ranged from 0.56 to 0.86 L/min for the organic output stream and 0.7 to 1.08 L/min for the aqueous extract. In all experiments the overall mass balance was 98.7% or better. The hexanol feed contained 34.28 to 37.88 g/L levulinic acid and 2.03 to 3.99 g/L hexyl levulinate, as measured by GC. Outlet flows of organic and aqueous phases from the unit were measured using timed volume collection. The unit was allowed to reach equilibrium by allowing three unit volumes of aqueous and organic phases to flow through the unit at a constant flowrate. Once at steady state, the flowrates of the organic and aqueous outlet streams were measured and samples of both streams were analyzed. Summaries of the streams are presented in Table 6. The results are summarized in Table 7.

In all experiments the extent of hexyl levulinate hydrolysis ranged from 19% to 36%. The extraction efficiency of levulinic acid into the aqueous extract phase over the four mixer-settler stages ranged from 73% to 88%.

The aqueous phase has not only hydrolyzed a significant portion of the hexyl levulinate fed to the unit but had extracted a high percentage of the available levulinic acid as an aqueous solution.

A number of embodiments of the invention have been described. Nevertheless, it will be understood that various modifications may be made without departing from the spirit and scope of the invention. Accordingly, other embodiments are within the scope of the following claims.

What is claimed is:
1. A method of producing levulinic acid, comprising:
contacting a first solution comprising levulinic acid and an acid with an organic solvent;
extracting at least a portion of the levulinic acid from the first solution into the organic solvent forming a second solution comprising an ester of levulinic acid and the organic solvent;

TABLE 6

Summary of input and output streams

| | Exp. 1 | Exp. 2 | Exp. 3 | Exp. 4 | Exp. 5 | Exp. 6 | Exp. 7 |
|---|---|---|---|---|---|---|---|
| Organic input stream | | | | | | | |
| Volumetric flow (LPM) | 0.6 | 0.55 | 0.78 | 0.84 | 0.63 | 0.59 | 0.62 |
| Mass flow (g/min) | 484.8 | 444.4 | 630.24 | 678.72 | 509.04 | 476.72 | 500.96 |
| Levulinic acid (g/L) | 37.88 | 37.88 | 37.88 | 37.88 | 34.28 | 34.28 | 34.28 |
| Hexyl levulinate (g/L) | 3.99 | 3.99 | 3.99 | 3.99 | 2.03 | 2.03 | 2.03 |
| Levulinic acid (g/min) | 22.73 | 20.83 | 29.55 | 31.82 | 21.60 | 20.23 | 21.25 |
| Hexyl levulinate (g/min) | 2.39 | 2.19 | 3.11 | 3.35 | 1.28 | 1.20 | 1.26 |
| Fresh water input stream | | | | | | | |
| Volumetric flow (LPM) | 0.76 | 0.84 | 1.09 | 1.11 | 0.75 | 0.71 | 0.72 |
| Mass flow (g/min) | 760 | 840 | 1090 | 1110 | 750 | 710 | 720 |
| Organic output stream | | | | | | | |
| Volumetric flow (LPM) | 0.61 | 0.56 | 0.79 | 0.86 | 0.64 | 0.6 | 0.63 |
| Mass flow (g/min) | 492.88 | 452.48 | 638.32 | 694.88 | 517.12 | 484.8 | 509.04 |
| Levulinic acid (g/L) | 0.64 | 0.64 | 0.62 | 0.78 | 0.3 | 0.58 | 0.84 |
| Hexyl levulinate (g/L) | 2.58 | 2.64 | 2.52 | 2.7 | 1.6 | 1.56 | 1.61 |
| Levulinic acid (g/min) | 0.39 | 0.36 | 0.49 | 0.67 | 0.19 | 0.35 | 0.53 |
| Hexyl levulinate (g/min) | 1.57 | 1.48 | 1.99 | 2.32 | 1.02 | 0.94 | 1.01 |
| Water output stream | | | | | | | |
| Volumetric flow (LPM) | 0.74 | 0.82 | 1.06 | 1.08 | 0.73 | 0.69 | 0.7 |
| Mass flow (g/min) | 740 | 820 | 1060 | 1080 | 730 | 690 | 700 |
| Levulinic acid (g/L) | 23.87 | 23.82 | 24.52 | 26.49 | 24.04 | 26.03 | 27.02 |
| Levulinic acid (g/min) | 17.66 | 19.53 | 25.99 | 28.61 | 17.55 | 17.96 | 18.91 |

TABLE 7

Summary of Results

| | Exp. 1 | Exp. 2 | Exp. 3 | Exp. 4 | Exp. 5 | Exp. 6 | Exp. 7 |
|---|---|---|---|---|---|---|---|
| Aq./Org. flow ratio | 1.3 | 1.5 | 1.4 | 1.3 | 1.2 | 1.2 | 1.2 |
| Hexyl levulinate hydrolyzed (g) | 0.82 | 0.72 | 1.12 | 1.02 | 0.25 | 0.26 | 0.24 |
| Hexyl levulinate hydrolyzed (%) | 34 | 33 | 36 | 31 | 20 | 22 | 19 |
| Levulinic acid extracted (%) | 73 | 88 | 83 | 85 | 79 | 86 | 86 |
| Overall mass balance (%) | 1.0 | 0.9 | 1.3 | 0.8 | 0.9 | 1.0 | 1.0 | contacting the second solution with water;
converting at least a portion of the ester of levulinic acid into levulinic acid; and
extracting at least a portion of the levulinic acid from the second solution into the water forming a third solution comprising the levulinic acid and the water,
wherein:
the first and third solutions are aqueous solutions; and
the organic solvent comprises hexanol.

2. The method of claim 1, wherein the acid comprises a member selected from the group consisting of sulfuric acid, nitric acid, hydrochloric acid, hydrobromic acid, and p-toluene sulfonic acid.

3. The method of claim 1, wherein the ester of levulinic acid comprises hexyl levulinate.

4. The method of claim 1, wherein the first solution comprises a volatile component, and the method further comprises removing the volatile component from the first solution.

5. The method of claim 1, further comprising contacting a precursor material with the acid to form the first solution.

6. The method of claim 5, wherein the precursor material comprises at least one member selected from the group consisting of cellulose, lignocellulose, furfural, furfuryl alcohol, and a sugar.

7. The method of claim 1, further comprising evaporating a portion of the water in the third solution.

8. The method of claim 7, wherein a concentration of levulinic acid in the third solution is from 60 wt. % to 90 wt. % after evaporation.

9. The method of claim 7, further comprising converting at least a portion of the levulinic acid into a member selected from the group consisting of ethyl levulinate, aminolevulinic acid, succinic acid, acrylic acid, 3-hydroxy propionic acid, and diphenolic acid.

10. The method of claim 1, further comprising separating the second solution from an aqueous phase.

11. The method of claim 1, further comprising separating the third solution from an organic phase.

12. The method of claim 1, wherein a ratio of water to second solution is from 0.25:1 to 5:1 water: second solution by weight.

13. A method of recovering levulinic acid, comprising:
contacting a first solution comprising an organic solvent and an ester of levulinic acid with water;
converting at least a portion of the ester of levulinic acid into levulinic acid; and
forming a second solution comprising levulinic acid and the water, wherein organic solvent comprises hexanol.

14. The method of claim 13, wherein the ester of levulinic acid comprises an ester formed from the reaction of levulinic acid and the hexanol.

15. The method of claim 13, wherein the ester of levulinic acid comprises hexyl levulinate.

16. The method of claim 13, further comprising evaporating a portion of the water in the second solution.

17. The method of claim 16, wherein a concentration of levulinic acid in the second solution is from 60% wt. % to 90 wt. % after evaporation.

18. The method of claim 16, further comprising converting at least a portion of the levulinic acid into a member selected from the group consisting of ethyl levulinate, aminolevulinic acid, succinic acid, acrylic acid, 3-hydroxy propionic acid, and diphenolic acid.

19. The method of claim 13, further comprising separating the second solution from an organic phase.

20. The method of claim 13, wherein a ratio of the water to first solution is from 0.25:1 to 5:1 water: first solution by weight.

21. The method of claim 1, wherein the second solution further comprises levulinic acid.

22. The method of claim 13, wherein the first solution further comprises levulinic acid.

23. The method of claim 4, wherein the volatile component comprises a member selected from the group consisting of formic acid, acetic acid, and furfural.

24. The method of claim 1, wherein the first solution comprises a solid component, and the method further comprises removing the solid component from the first solution.

25. The method of claim 24, wherein the solid component is removed using a removal method selected from the group consisting of filtration, centrifugation, and sedimentation.

* * * * *